United States Patent
Yamaguchi

US006921471B2

(10) Patent No.: US 6,921,471 B2
(45) Date of Patent: Jul. 26, 2005

(54) GEL PROCESS PLATE

(75) Inventor: Ryo Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 827 days.

(21) Appl. No.: 09/845,326

(22) Filed: May 1, 2001

(65) Prior Publication Data
US 2002/0009396 A1 Jan. 24, 2002

(30) Foreign Application Priority Data

May 31, 2000 (JP) .......................................... 2000-162772

(51) Int. Cl.$^7$ ................................................. C25B 9/18
(52) U.S. Cl. ........................ 204/606; 204/619; 204/618
(58) Field of Search ................................. 204/606, 618, 204/619

(56) References Cited

U.S. PATENT DOCUMENTS 4,882,127 A * 11/1989 Rosenthal et al. ............ 422/50
5,785,835 A * 7/1998 Saito et al. ................ 204/616

* cited by examiner

*Primary Examiner*—Ling-Sui Choi
(74) *Attorney, Agent, or Firm*—Manabu Kanesaka

(57) ABSTRACT

A gel process plate is formed of a base member with a plurality of concave portions, and a lid member with a plurality of convex portions. Each concave portion has a bottom surface provided with holes for allowing a liquid to pass therethrough. Each convex portion has a height less than a depth of the concave portion of the base member, and a top surface with holes for allowing the liquid to pass therethrough. The convex portions are disposed at portions corresponding to the concave portions of the base member to fit the concave portions. When the base member and the lid member are assembled, a space is defined between the bottom surface of the concave portion and the top surface of the convex portion to hold a piece, i.e. gel piece, therein for processing.

5 Claims, 2 Drawing Sheets

Fig. 1(d)

GEL PROCESS PLATE

BACKGROUND OF THE INVENTION AND RELATED ART STATEMENT

The present invention relates to an instrument or device for a gel process used in a field of an analytical technology in the chemistry and the biotechnology, and more specifically, the present invention relates to an instrument or device used in a process for splitting an objective biopolymer from a gel after the biopolymer, such as protein or DNA, is separated by an electrophoresis by using slab-like gel.

In order to provide a biopolymer as a sample for analyzing means by splitting the biopolymer existing in a desired electrophoresis pattern from a slab-like gel in which the biopolymer is separated by an electrophoresis, a desired portion of the slab-like gel, in which the separation of the biopolymer is completed by the electrophoresis, is cut or hollowed out. Then, the biopolymer is recovered from the cut-out or hollowed-out gel piece by a chemical process by a proteolytic enzyme or the like and an extraction, and these processes are carried out by a manual operation or by using various robots. The extracted biopolymer is provided as a sample to the analyzing means.

In the operation of recovering the objective biopolymer from the gel piece, a microtube 2 as shown in FIG. 3 or the like is used. The cut-out gel piece 4 is inserted into the microtube 2, and respective steps, such as wetting or humectation into various solutions 8, taking out the solution, and drying, are carried out by a micro-tip 6 or micro-pipette provided at a distal end of a nozzle. In this case, in the respective steps, it is necessary to proceed the operations or works without damaging the gel piece while the gel piece is prevented from closing the tip or the nozzle.

In case the biopolymer is recovered from the gel piece, in the several steps of humectation or soaking into the various solutions and drying, which are carried out until the final step of extracting the biopolymer into a solution, the biopolymer is chemically processed in the condition that the biopolymer is adsorbed to the gel piece.

Since the operation of recovering the objective biopolymer from the gel piece after being electrophoresed is cumbersome, automation is demanded for the purpose of mass processing. However, if a separation and infusing mechanism using the micro-pipette or the nozzle is used for carrying out discharge and suction of the solution, due to a dispersion of the gel or a contamination of bubbles at the time of discharging the solution, the gel piece may not be completely soaked in the solution, or the gel may close the tip or the nozzle in case of sucking the solution. In order to avoid the above incidents, the pipette operation is required to be conducted while avoiding the gel piece. However, such a demand prevents the automation of the operation, and even if the operation is conducted manually, skill is required for the aforementioned operation.

Regarding the suction of the solution, there is a method of sucking the solution from a bottom surface of a container by using a filter or the like without using the nozzle. However, if a solution suction unit by a pressure reduction described above is provided, the device becomes large.

Accordingly, an object of the invention is to provide an instrument or device which can easily conduct a chemical process before the final step of abstracting biopolymers into a solution in an operation of recovering an objective biopolymer from a cut-out gel piece.

Further objects and advantages of the invention will be apparent from the following description of the invention.

SUMMARY OF THE INVENTION

A device of the invention is a plate for processing gel pieces by accommodating the same, and the gel process plate of the invention comprises: a base member which can accommodate gel pieces cut out from a slab-like gel in which a separation of biopolymers as a sample is completed by an electrophoresis, wherein the base member has a plurality of concave portions including bottom surfaces with holes for allowing a liquid to pass therethrough; and a lid member which has a plurality of convex portions including top surfaces with holes for allowing a liquid to pass therethrough, and heights lower than the depths of the concave portions. The convex portions are formed at positions corresponding to the concave portions of the base member and are fitted in the concave portions to cover the same.

In the condition that the lid member and the base member are assembled with each other by fitting the convex portions of the lid member with the concave portions of the base member, the gel pieces are held in the spaces between the bottom surfaces of the concave portions of the base member and the top surfaces of the convex portions of the lid member. Wetting or soaking of the gel pieces into solutions for chemical processing until extraction for recovering the biopolymers from the gel pieces, can be conducted by soaking the plate in the condition of storing the gel pieces therein into the solution. Also, in order to exchange the solutions, the gel pieces stored in the plate are taken out from a vessel as they are, and can be soaked into another vessel. Alternatively, in the condition that the plate is soaked in the vessel, the solution of the vessel can be exchanged in order to replace the solutions.

In the step of chemical processing of the gel pieces by using the plate, the biopolymers adsorbed in the gel pieces are not extracted into the solutions yet, and there is maintained a condition that the biopolymers are adsorbed in the gel pieces. Therefore, even if a plurality of gel pieces adsorbing different biopolymers is accommodated in a single plate and chemically processed at the same time, there is no problem.

As described above, since the chemical processes are conducted in the condition that the gel pieces are accommodated in the plate, as compared with the conventional method in which the chemical processes are conducted by using the separation and infusion mechanism, the gel pieces can be securely soaked in the solutions. Also, since the removal of the gel pieces from the solution and drying can be conducted in the condition that the gel pieces are accommodated in the plate, a cumbersome operation such that the nozzle or the tip is inserted to a position away from the gel pieces, is not required.

BRIEF DESCRIPTION OF THE DRAWINGS

FIGS. 1(a) through 1(d) show an embodiment of the invention, wherein FIG. 1(a) is a plan view of a lid member; FIG. 1(b) is a schematic sectional view of the lid member; FIG. 1(c) is a schematic sectional view of a base member; and FIG. 1(d) is a schematic sectional view of the lid member and the base member assembled together;

DETAILED DESCRIPTION OF PREFERRED EMBODIMENTS

Hereinafter, an embodiment of the invention will be explained with reference to the attached drawings. FIGS.

Figure 1A:
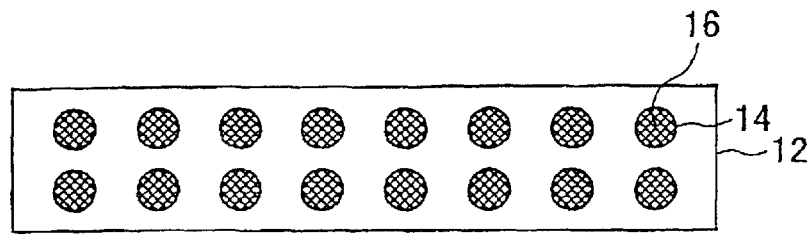
Figure 1B:
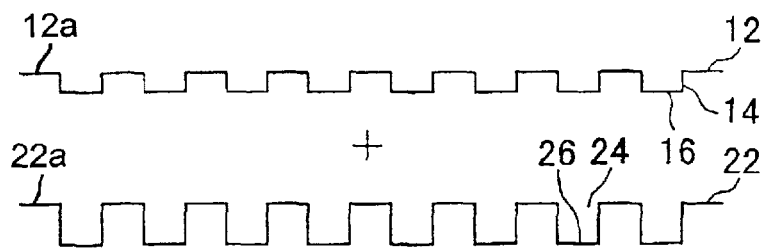
Figure 1C:
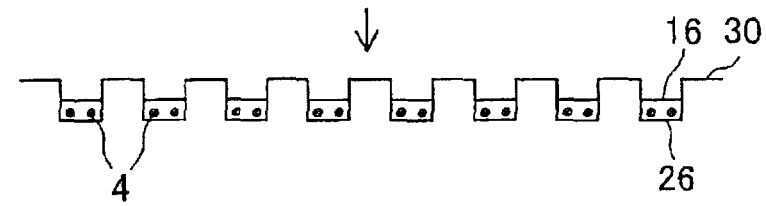

1(a) through 1(d) show an embodiment of the invention including gel holding sections arranged in eight columns and two rows. FIG. 1(a) is a plan view of a lid member 12; FIG. 1(b) schematically shows a section of the lid member 12 which is cut at a position of convex portions 14; and FIG. 1(c) schematically shows a section of a base member 22 which is cut at a position of concave portions 24. A plan view of the base member 22 is substantially the same as that shown in FIG. 1(a).

In the base member 22, there are formed a top surface 22a and a plurality of cylindrical concave portions 24, and at the bottom surfaces 26 of the concave portions 24, there are formed grid-like holes which allow a liquid to pass therethrough. In the lid member 12, there are formed a top surface 12a and cylindrical convex portions 14 provided at positions corresponding to the respective concave portions 24 in order to assemble the lid member 12 with the base member 22. At the top surfaces 16 of the convex portions 14, there are formed grid-like holes which allow the liquid to pass therethrough. An external dimension of the convex portion 14 is set at a size such that a space is formed between the bottom surface 26 of the concave portion 24 and the top surface 16 of the convex portion 14 by fitting the convex portion 14 with an inner side of the concave portion 24 to cover an opening of the convex portion 24 when the base member 22 and the lid member 12 are assembled.

FIG. 1(d) is a schematic end view of a section of a plate 30 in which the base member 22 and the lid member 12 are assembled, wherein the plate 30 is cut at positions of the convex portions 14 and the concave portions 24 as in FIGS. 1(b) and 1(c). FIG. 1(d) shows a condition that gel pieces 4 are stored in the spaces between the bottom surfaces 26 of the concave portions 24 and the top surfaces 16 of the convex portions 14.

The base member 22 and the lid member 12 are plastic molded members, and have sizes in the order of a micro-titre plate. However, this is just an example, and materials and sizes thereof are not limited to the above.

In explaining the operations of the embodiment, the gel pieces 4 are respectively inserted in the concave portions 24 of the base member 22, and the lid member 12 is put on the concave portions 24 from above so that the convex portions 14 are fitted in the concave portions 24 to thereby cover the concave portions 24 with the convex portions 14, resulting in assembling the base member 22 with the lid member 12. Accordingly, since the gel pieces 4 are confined in the spaces between the top surfaces 16 and the bottom surfaces 26, which are respectively provided with grid-like holes, from upper sides and lower sides of the gel pieces, steps of chemical processes which follow thereafter are conducted in the condition that the gel pieces 4 are held in the spaces described above.

Figure 2:
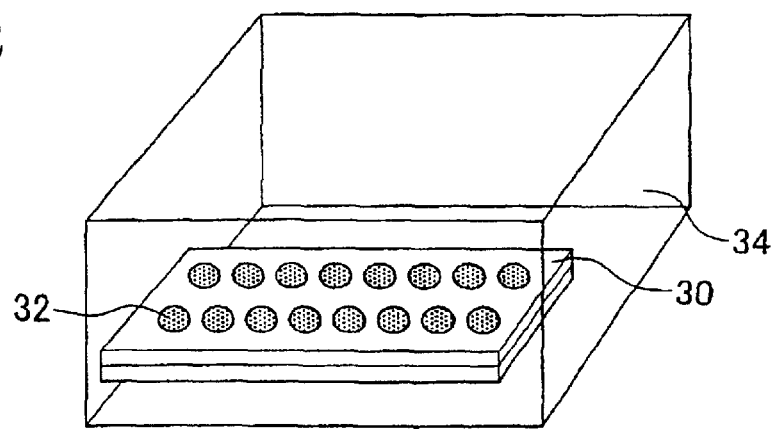
FIG. 2 is a schematic perspective view showing a condition that plate holding gel pieces are soaked in a vessel.
Figure 3:
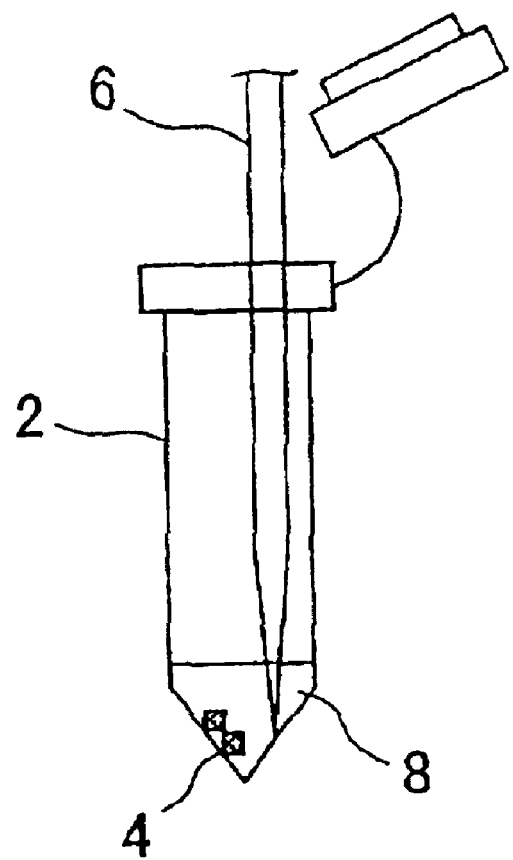
FIG. 3 is a schematic sectional view showing a conventional method of recovering an objective biopolymer from gels by using a microtube.

FIG. 2 shows a condition that the plate 30, in which the base member 22 and the lid member 12 hold the gel pieces 4 therebetween and are assembled with each other, is soaked in a vessel 34. Reference numeral 32 designates a gel holding section which holds the gel piece 4 in the plate 30. Exchange of the solution is conducted by exchanging the solution in the vessel 34 in the condition that the plate 30 holding the gel pieces 4 is kept in the vessel 34, or by taking out the plate 30 in the condition of holding the gel pieces from one vessel to transfer the plate 30 to another vessel.

Although the embodiment shows the plate which has the gel holding sections arranged in eight columns and two rows, a number of the gel holding sections, and shapes or sizes of the holes for allowing the solutions therethrough are not limited to those in the embodiment. Further, although it is easy to automatically conduct the steps of exchanging the solution and drying in case that the chemical processing is conducted by soaking the plate, the plate of the invention can be utilized in case those steps are manually operated.

Also, kinds of the gels to which the chemical process is applied by using the plate of the invention, kinds of the sample extracted after the gel is separated by the electrophoresis and chemically processed by using the plate of the invention, and contents of the chemical processing for recovering the sample are not limited to those in the aforementioned embodiment.

The present invention constitutes a plate formed of a base member, which has a plurality of concave portions including bottom surfaces with holes for allowing a liquid to pass therethrough, and a lid member, which has convex portions including heights less than the depths of the concave portions of the base member and provided with the top surfaces with holes for allowing the liquid to pass therethrough, in which the convex portions fitted as the lids into the concave portions of the base member are formed at positions respectively corresponding to the concave portions of the base member. The plate is structured such that the chemical process can be applied to the gel pieces in the condition that the gel pieces are accommodated in the spaces between the bottom surfaces of the concave portions of the base member and the top surfaces of the convex portions of the lid member.

In the digestion steps in which the protein separated by the electrophoresis is digested in the gel, in the condition that the gel is soaked in the solution, for example, in a condition that a micro-titre plate itself is fitted into a temperature controlling block, or in a condition that the microtube is inserted into a hole formed in the temperature controlling block, a temperature of the temperature controlling block may be controlled, to thereby incubate at a certain temperature. In this case, a temperature locality tends to appear. However, by using the plate of the invention, the plate holding the gel pieces is soaked in the vessel, and a temperature of the vessel including the plate is controlled, so that the temperature locality can be reduced, resulting in increasing the stability of the result.

Also, a plurality of plates can be arranged side by side in the single vessel, so that the space can be effectively used.

Furthermore, it is easy to apply an ultrasonic treatment for infiltrating the solution into the gel sufficiently.

While the invention has been explained with reference to the specific embodiments of the invention, the explanation is illustrative and the invention is limited only by the appended claims.

What is claimed is:

1. A gel process plate, comprising:
    a base member including a plurality of concave portions, each having a depth and a bottom portion provided with holes for allowing a liquid to pass therethrough, and
    a lid member including a plurality of convex portions, each having a height less than the depth of the concave portion of the base member, and a top portion with holes for allowing the liquid to pass therethrough, said convex portions being formed at portions corresponding to the concave portions of the base member to fit the concave portions so that when the base member and the lid member are assembled, a space is defined between each of the bottom portion of the concave portion and each of the top portion of the convex portion to hold a piece therein for processing while allowing the liquid to pass through the holes of the top and bottom portions.

2. A gel process plate according to claim 1, wherein said piece is a gel piece cut out from a slab-like gel in which a separation of biopolymers is completed by an electrophoresis.

3. A gel process plate according to claim 1, wherein said base member has a flat top surface and each concave portion has a side wall extending downwardly from the top surface; and said lid member has a flat top surface and each convex portion has a side wall extending downwardly from the top surface.

4. A gel process plate according to claim 3, wherein when the base member and the lid member are closed, the flat top surfaces of the base member and the lid member contact each other and the spaces are formed between the concave portions and convex portions.

5. A gel process plate according to claim 1, wherein each of said top portions with the holes of the convex portions and the bottom portions with the holes of the concave portions has a grid shape.

* * * * *